United States Patent [19]

Kuwada et al.

[11] 4,046,772

[45] Sept. 6, 1977

[54] BENZODIAZEPINE DERIVATIVE AND PROCESS FOR PRODUCING THE SAME

[75] Inventors: Yutaka Kuwada, Ashiya; Hiroyuki Tawada, Takatsuki; Kanji Meguro, Takarazuka, all of Japan

[73] Assignee: Takeda Chemical Industries, Ltd., Osaka, Japan

[21] Appl. No.: 566,434

[22] Filed: Apr. 9, 1975

[30] Foreign Application Priority Data

Apr. 12, 1974 Japan .................... 49-41229

[51] Int. Cl.$^2$ .................... C07D 487/14
[52] U.S. Cl. .................... 260/308 R; 260/243.3; 260/268 TR; 260/293.59; 424/248.54; 424/250; 424/267; 424/269
[58] Field of Search .............. 260/247.2 B, 247.5 EP, 260/268 TR, 293.59, 308 R

[56] References Cited

U.S. PATENT DOCUMENTS

| | | | |
|---|---|---|---|
| 3,681,343 | 8/1972 | Hester | 260/308 R |
| 3,703,525 | 11/1972 | Tawada et al. | 260/308 R |
| 3,862,171 | 1/1975 | Gagneux et al. | 260/308 R |
| 3,870,714 | 3/1975 | Gagneux et al. | 260/293.59 |
| 3,907,820 | 9/1975 | Meguro et al. | 260/308 R |

Primary Examiner—Raymond V. Rush
Attorney, Agent, or Firm—Burgess, Ryan and Wayne

[57] ABSTRACT

A benzodiazepine derivative of the general formula:

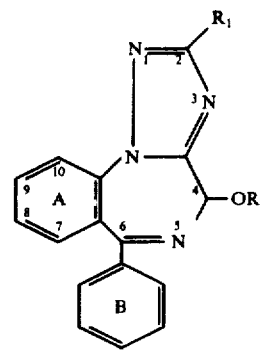

wherein $R_1$ represents a hydrogen atom, an alkyl group or a carboxyl group which may be esterified or amidated; R represents a hydrogen atom, an acyl group or a lower alkyl group, and each of the rings A and B is unsubstituted or substituted by halogen atom, nitro, lower alkyl, trifluoromethyl or lower alkoxy group, or its pharmaceutically acceptable acid addition salt is found to be useful as medicine in human and animal therapy, which acts on the central nervous system, e.g. muscle relaxants, anticonvulsants, sedatives, tranquilizers etc.

17 Claims, No Drawings

BENZODIAZEPINE DERIVATIVE AND PROCESS FOR PRODUCING THE SAME

This invention relates to a pharmaceutically useful benzodiazepine derivative of the general formula (I):

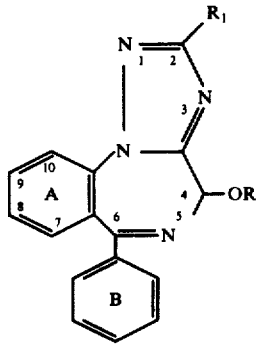

(I)

wherein $R_1$ represents a hydrogen atom, an alkyl group or a carboxyl group which may be esterified or amidated; R represents hydrogen atom, an acyl group, or a lower alkyl group, and each of the rings A and B is unsubstituted or substituted by halogen atom, nitro, lower alkyl, trifluoromethyl or lower alkoxy group or its pharmaceutically acceptable acid addition salt, and to processes for producing the same.

The following classes of compounds (I-a), (I-b) and (I-c) are included within the scope of the compound (I) of the present invention:

a. Compound (I) wherein R is an acyl group represented by -COR$_6$:

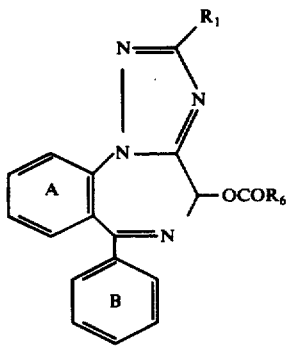

(I-a)

wherein $R_6$ represents an alkyl, aryl or aralkyl group, and the rings A and B and other symbols are as defined above;

b. compound (I) wherein R is a hydrogen atom:

(I-b)

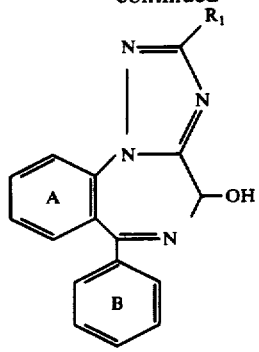

wherein the rings A and B, and all symbols are as defined above; and c. compound (I) wherein R is a lower alkyl group represented by $R_2$:

(I-c)

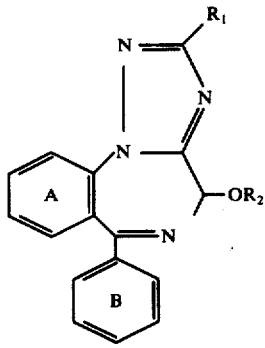

wherein $R_2$ represents a lower alkyl group, and the rings A and B and other symbols are as defined above.

The alkyl group represented by $R_1$ in the above formulae may be lower alkyls having 1 to 6 carbon atoms, and the alkyl group may be straight, branched or cyclic. Examples thereof are methyl, ethyl, propyl, isopropyl, butyl, isobutyl, sec-butyl, tert-butyl, cyclopropylmethyl, pentyl, cyclopentyl, hexyl, cyclohexyl, etc., among which lower alkyl groups having 1 to 3 carbon atoms are preferred. When the carboxyl group represented by R1 is esterified, it is represented by the general formula —COOR$_3$, wherein $R_3$ represents a lower alkyl group having 1 to 4 carbon atoms among the alkyl groups as represented by $R_1$. Furthermore, when the carboxyl group represented by $R_1$ is amidated, it is represented by the general formula

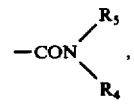

wherein each of $R_4$ and $R_5$ represents hydrogen atom or an alkyl group which may have a lower alkoxy group as substituents and they may form a heterocyclic ring together with the nitrogen atom adjacent thereto. As the alkyl groups represented by $R_4$ and $R_5$, there are lower alkyl groups having 1 to 6 carbon atoms such as the alkyl groups represented by $R_1$, among which lower alkyls having 1 to 3 carbon atoms are preferred. When the alkyl groups represented by $R_4$ and $R_5$ have lower alkoxy group as substituent, said alkoxy groups are preferably lower ones having 1 to 4 carbon atoms such as methoxy, ethoxy, propoxy, isopropoxy, butoxy, etc. When the alkyl groups represented by $R_4$ and $R_5$ have these alkoxy groups as substituents, they may be substituted by one or more of these substituents at optional positions of the alkyl group. Examples of such substituted alkyl groups represented by $R_4$ and $R_5$ are 2-methoxyethyl, 2-ethoxyethyl, 2,2-dimethoxyethyl, 2,2-diethoxyethyl, 3-methoxypropyl, 3-ethoxypropyl, 2-methoxypropyl, 2-ethoxypropyl, etc. When $R_4$ and $R_5$ form a heterocyclic ring together with the nitrogen atom adjacent thereto, such heterocyclic ring is preferably a five to seven membered ring, which may contain another 1 to 2 nitrogen and/or oxygen atoms, etc. as hereto atoms and this heterocyclic ring may further be substituted at optional position with the same alkyl or alkoxyalkyl groups as those represented by $R_4$ and $R_5$. Examples of such heterocyclic rings are pyrrolidine, piperidine, homopiperidine, morpholine, N-mono-substituted piperazine (e.g., N-methyl-, N-ethyl, N-propyl-, N-(2-methoxyethyl)-piperazine), etc. Among the substituents represented by $R_1$, the amidated carboxyl group, especially carboxamide group, is preferable.

Preferred alkyl groups represented by $R_2$ are straight or branched lower alkyl groups having 1 to 4 carbon atoms such as methyl, ethyl, propyl, isopropyl, butyl, isobutyl, sec-butyl, tert-butyl, etc. The acyl group represented by R is represented by the formula -$COR_6$, wherein $R_6$ represents alkyl, aryl or aralkyl group. The alkyl groups represented by $R_6$ are exemplified by lower alkyl group having 1 to 4 carbon atoms which are the same as those represented by $R_2$. The aryl groups represented by $R_6$ are exemplified by phenyl, tolyl, etc., and the aralkyl groups represented by $R_6$ are exemplified by benzyl, phenethyl, etc. Among the acyl groups represented by R, those of the general formula —$COR_6$ wherein $R_6$ is the lower alkyl are preferable.

When the rings A and/or B are substituted by one or more, being same or different, halogen atom, nitro, lower alkyl, trifluoromethyl or lower alkoxy group, these substituents may occupy at optional position or positions of the rings A and/or B. Examples of the halogen atom, which may be the substituents on the ring A and/or B are fluorine, chlorine, bromine and iodine, and examples of the alkyl group are the same lower alkyl groups having 1 to 4 carbon atoms as those represented by $R_2$. Examples of the alkoxy group are the same lower alkoxy group having 1 to 4 carbon atoms as those, which may be the substituents on the alkyl groups represented by $R_4$ and $R_5$. As the substituent(s) of the rings A and/or B, halogen atom(s), especially halogen atom at 8-position of the ring A and/or halogen atom or atoms at ortho-position or positions of the ring B, are preferable.

In the formulae described hereinafter, the rings A and B and all the symbols have the same meanings as defined above;

The class of the compounds (I-a) of the present invention can be produced by the following processes:

a. a process which comprises (step A) reacting a compound of the general formula (II):

(II)

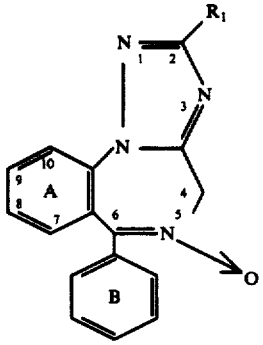

with a reactive derivative of a carboxylic acid of the general formula $R_6COOH$; and b. a process which comprises (step E) reacting a compound of the general formula (I-b):

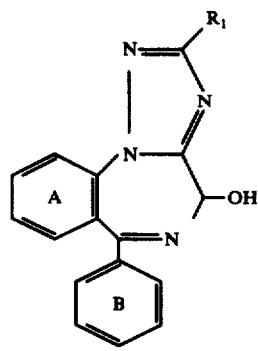

(I-b)

with an esterifying agent capable of converting the hydroxyl group at 4-position of the compound (I-b) into acyloxy group of the general formula —$COR_6$.

The class of the compounds (I-b) of the present invention can be produced by the following processes:

c. a process which comprises (step C) subjecting a compound of the general formula (I-a):

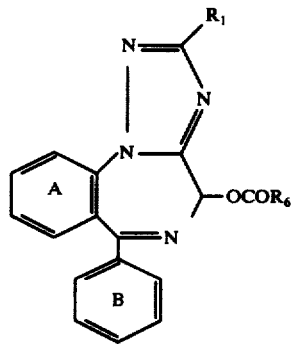

(I-a)

to hydrolysis; and d. a process which comprises (step A) reacting a compound of the general formula (II):

(II)

-continued

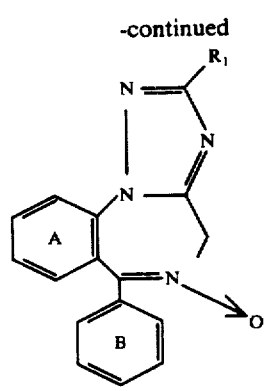

with a reactive derivative of a carboxylic acid of the general formula R₆COOH to produce a compound of the general formula (I-a):

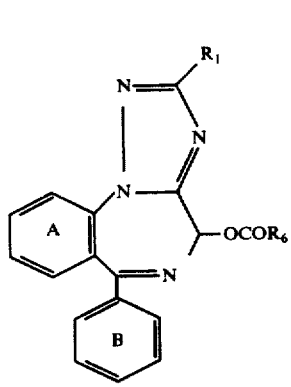
(I-a)

and then (step C) subjecting the thus obtained compound to hydrolysis.

The class of the compounds (I-c) of the present invention can be produced by the following processes:

e. a process which comprises (step B) reacting a compound of the general formula (I-a):

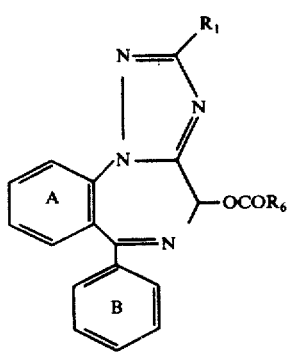
(I-a)

with a compound of the general formula R₂OH.

f. a process which comprises (step A) reacting a compound of the general formula (II):

(II)

-continued

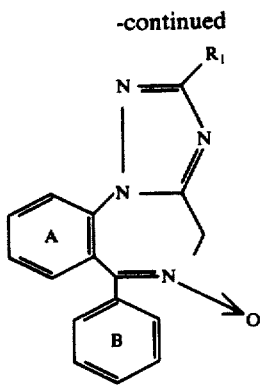

with a reactive derivative of a carboxylic acid of the general formula R₆COOH to produce a compound of the general formula (I-a):

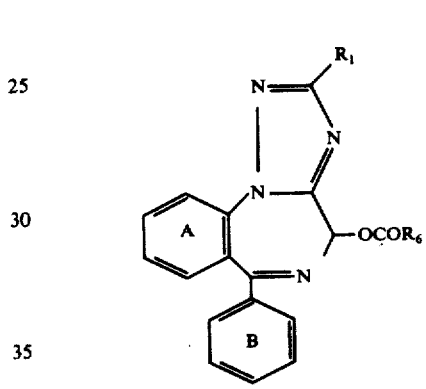
(I-a)

and then (step B) reacting the thus obtained compound with a compound of the general formula R₂OH.

g. a process which comprises (step D) reacting a compound of the general formula (I-b):

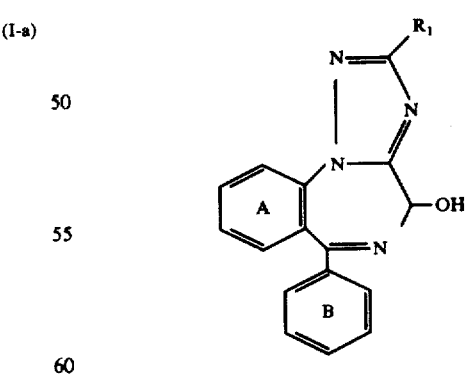
(I-b)

with a compound of the general formula R₂OH.

h. a process which comprises (step C) subjecting a compound of the general formula (I-a):

(I-a)

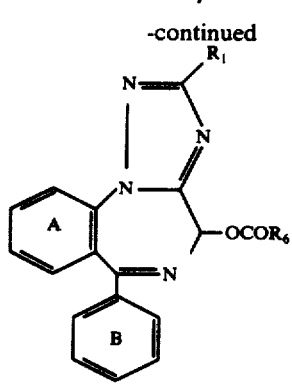

to hydrolysis to produce a compound of the general formula (I-b):

(I-b)

and then (step D) reacting the thus obtained compound with a compound of the general formula $R_2OH$; and i. a process which comprises (step A) reacting a compound of the general formula (II):

(II)

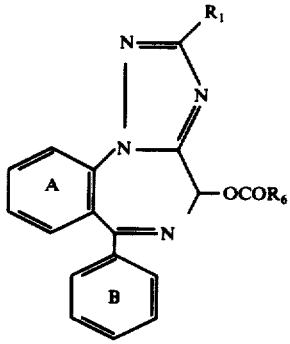

with a reactive derivative of a carboxylic acid of the general formula $R_6COOH$ to produce a compound of the general formula (I-a):

(I-a)

then (step C) subjecting the thus obtained compound to hydrolysis to produce a compound of the general formula (I-b):

(I-b)

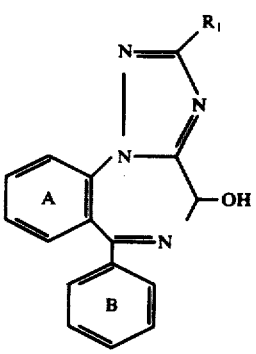

and further reacting the thus obtained compound with a compound of the general formula $R_2OH$.

The reactions involved in the processes of the present invention are summarized in the following reaction scheme:

(II)      (I-c)

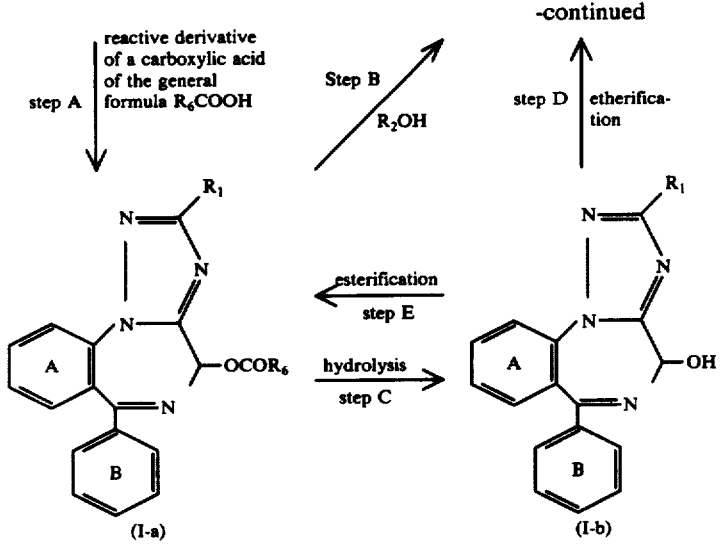

In the above reaction scheme, the rings A and B and all the symbols have the same meanings as defined above.

The reaction of the step A of this invention is carried out by reacting the compound of the general formula (II) with a reactive derivative of a carboxylic acid of the general formula $R_6COOH$. Examples of the reactive derivatives of carboxylic acid used in the reaction are acid halides of carboxylic acids represented by the general formula $R_6COOH$ (wherein $R_6$ is as defined above) (e.g., acid chlorides, acid bromides, etc.), acid anhydrides thereof, sulfides represented by $(R_6CO)_2S$, etc. Said reactive derivative of carboxylic acid is used usually in amounts of about 2 to 5 moles per mole of the compound (II).

The reaction is usually carried out at about 0 to 200° C in the presence of a solvent. As the solvents, for example, dimethylformamide, tertiary amines (e.g., pyridine, picoline), carboxylic acids represented by $R_6COOH$ may be used. Furthermore, when the reactive derivative of carboxylic acid used for the reaction is liquid, the reactive derivative may be used in an excess amount to allow the derivative itself to serve as the solvent. By the reaction of this step, there is produced the compound (I-a) in which an acyloxy group corresponding to the reactive derivative of carboxylic acid used (i.e., $—COR_6$) is introduced at 4-position of the starting compound (II).

The reaction of the step B is an alcoholysis of the compound (I-a). The alcoholysis of the compound (I-a) is conducted by reacting the alcohol of the formula $R_2OH$ with the compound (I-a). The amount of the alcohol to be used may be at least equimolar relative to the starting compound (I-a) and is not specifically limited. Usually, the reaction is conducted preferably in the presence of an acid and does not necessarily require solvent since the alcohol used also serves as a solvent, but halogenated hydrocarbons (e.g., chloroform, carbon tetrachloride) may be used as the solvent. The reaction temperature is generally between about room temperature to the boiling point of the alcohol and/or solvent to be used. The acid to be used in the reaction is exemplified by mineral acids (e.g., hydrochloric acid, sulfuric acid), inorganic acids (e.g., phosphoric acid), carboxylic acids (e.g., acetic acid, propionic acid), and organic acids such as organic sulfonic acids (e.g., toluenesulfonic acid, methanesulfonic acid).

The reaction of the step C is a hydrolysis of the compound (I-a). The hydrolysis may be any one known per se which can convert the acyloxy group at 4-position of the compound (I-a) into hydroxyl group. For example, the hydrolysis is usually conducted by treating the compound (I-a) with a basic substance at about room temperature in the presence or absence of a solvent. The solvent is exemplified by lower alkanols (methanol, ethanol, propanol), dioxane, tetrahydrofuran, etc. If necessary, the reaction may be carried out under suitable heating (e.g., to boiling point of the solvent employed). The basic substance is exemplified by hydroxides or carbonates of alkali metals (e.g., sodium hydroxide, potassium hydroxide, sodium carbonate, potassium carbonate).

The reaction of the step D is an etherification of the compound (I-b). The etherification reaction is conducted by reacting the compound of the general formula (I-b) with an alcohol corresponding to $—OR_2$, preferably in the presence of an acid. As the alcohols and the acids, those used in the alcoholysis of the step B may also be used. The reactant alcohol may take a role as a solvent of reaction and therefore any other solvent is not especially required. However, there may be used the same solvents as used in the alcoholysis of the step B under the same reaction conditions as in said alcoholysis.

The reaction of step E is an esterification of the compound (I-b). The esterification is conducted by reacting an esterifying agent capable of converting the hydroxy group at 4-position of the compound (I-b) into acyloxy group with the compound of the general formula (I-b). As the esterifying aents, any of the reactive derivatives of carboxylic acid used in the step A may be used, usually in amounts of about 1 to 3 moles per mole of the starting compound. The reaction is generally carried out in the presence of a solvent at room temperature to about the boiling point of the solvent used. The solvents are exemplified by chloroform, pyridine, dimethylformamide, etc. and when the reactive derivatives of carboxylic acid used are liquid, they may be used in an excess amount to allow them to serve also as the solvent.

Furthermore, since the object compounds (I) of the present invention have basic nitrogen atoms in nucleus, they can be converted into corresponding acid addition salts by treatment with inorganic acids (e.g., hydrochloric acid, hydrobromic acid, sulfuric acid, nitric acid, phosphoric acid, etc.) or organic acids (e.g., oxalic acid, succinic acid, malonic acid, tartaric acid, fumaric acid, maleic acid, methanesulfonic acid, p-toluensulfonic acid, etc.) by conventional means (e.g., by heating the compound (I) with these acids in a solvent. The conversion into the acid addition salt may be carried out upon or after recovering the object compound (I).

The object compounds (I) or their acid addition salts thus prepared have pharmacological effects acting on the central nervous system, such as muscle relaxant, anticonvulsant, sedative, antianxiety, tranquilizing or sleep inducing effects and therefore are useful as medicines in human and animal therapy such as muscle relaxants, anticonvulsants, sedatives, minor tranquilizers, antianxiety agents and hypnotics. The compounds (I) and their pharmaceutically acceptable acid addition salts are orally or parenterally administrable as such or in a suitable form such as powder, granules, tablets, capsules or injectable solutions admixed with a pharmaceutically acceptable carrier, excipient or diluent. The dose of said compounds (I) or their salts to be administered varies with the kinds and severity of the disease and kinds of the compound or its salt and generally is about 0.1 to 50 mg for oral administration for an adult human per day.

The starting compound (II) of the present invention can be produced by the methods disclosed in Dutch Patent Application No. 7301601, Japanese Patent Application Laid Open No. 12219/1972 and French Pat. No. 7040746.

Specific compounds as represented by the general formula (I), inclusive of those as shown in Examples which are set forth for illustrative but not limiting purpose, are as follows;

1. 4-Hydroxy-6-phenyl-4H-s-triazo[1,5-a][1,4]benzodiazepine
2. 8-Chloro-4-hydroxy-6-phenyl-4H-s-triazolo[1,5-a][1,4]benzodiazepine
3. 8-Chloro-6-(2-chlorophenyl)-4-hydroxy-4H-s-triazolo[1,5-a][1,4]benzodiazepine
4. 8-Chloro-6-(2-chlorophenyl)-4-methoxy-4H-s-triazolo-[1,5-a][1,4]benzodiazepine
5. 8-Chloro-4-methoxy-6-phenyl-4H-s-triazolo[1,5-a][1,4]benzodiazepine
6. 8-Chloro-4-hydroxy-2-methyl-6-phenyl-4H-s-triazolo[1,5-a][1,4]benzodiazepine
7. 8-Chloro-6-(2-chlorophenyl)-4-methoxy-2-methyl-4H-s-triazolo[1,5-a][1,4]benzodiazepine
8. 8-Chloro-2-ethyl-4-methoxy-6-phenyl-4H-s-triazolo[1,5-a][1,4]benzodiazepine
9. 8-Chloro-6-(2-chloroethyl)-2-ethyl-4-methoxy-4H-s-triazolo[1,5-a][1,4]benzodiazepine
10. 8-Chloro-6-(2,6-difluorophenyl)-4-methoxy-4H-s-triazolo[1,5-a][1,4]-benzodiazepine-2-carboxamide
11. 8-Chloro-4-methoxy-6-phenyl-4H-s-triazolo[1,5-a][1,4]-benzodiazepine-2-carboxylic acid
12. Ethyl 8-chloro-4-methoxy-6-phenyl-4H-s-triazolo[1,5-a][1,4]benzodiazepine-2-carboxylate
13. Ethyl 8-chloro-6-(2-chlorophenyl)-4-methoxy-4H-s-triazolo[1,5-a][1,4]benzodiazepine-2-carboxylate
14. 8-Chloro-4-hydroxy-6-phenyl-4H-s-triazolo[1,5-a][1,4]benzodiazepine-2-carboxamide
15. 8-Chloro-6-(2-chlorophenyl)-4-hydroxy-4H-s-triazolo[1,5-a][1,4]benzodiazepine-2-carboxamide
16. 8-Chloro-4-methoxy-6-phenyl-4H-s-triazolo[1,5-a][1,4]benzodiazepine-2-carboxamide
17. 8-Chloro-6-(2-chlorophenyl)-4-methoxy-4H-s-triazolo[1,5-a][1,4]benzodiazepine-2-carboxamide
18. 8-Chloro-4-hydroxy-N-methyl-6-phenyl-4H-s-triazolo[1,5-a][1,4]benzodiazepine-2-carboxamide
19. 8-Chloro-6-(2-chlorophenyl)-4-methoxy-N-methyl-4H-s-triazolo[1,5-a][1,4]benzodiazepine-2-carboxamide
20. 8-Chloro-4-hydroxy-N,N-dimethyl-6-phenyl-4H-s-triazolo[1,5-a][1,4]benzodiazepine-2-carboxamide
21. 8-Chloro-6-(2-chlorophenyl)-4-methoxy-N,N-dimethyl-4H-s-triazolo[1,5-a][1,4]benzodiazepine-2-carboxamide
22. 8-Chloro-4-hydroxy-6-phenyl-2-piperidinocarbonyl-4H-s-triazolo[1,5-a][1,4]benzodiazepine
23. 8-Chloro-6-(2-chlorophenyl)-4-hydroxy-2-piperidinocarbonyl-4H-s-triazolo[1,5-a][1,4]benzodiazepine
24. 8-Chloro-4-methoxy-6-phenyl-2-piperidinocarbonyl-4H-s-triazolo[1,5-a][1,4]benzodiazepine
25. 8-Chloro-6-(2-chlorophenyl)-4-methoxy-2-piperidinocarbonyl-4H-s-triazolo[1,5-a][1,4]benzodiazepine
26. 8-Chloro-4-hydroxy-2-morpholinocarbonyl-6-phenyl-4H-s-triazolo[1,5-a][1,4]benzodiazepine
27. 8-Chloro-6-(2-chlorophenyl)-4-hydroxy-2-morpholinocarbonyl-4H-s-triazolo[1,5-a][1,4]benzodiazepine
28. 8-Chloro-4-methoxy-2-morpholinocarbonyl-6-phenyl-4H-s-triazolo[1,5-a][1,4]benzodiazepine
29. 8-Chloro-6-(2-chlorophenyl)-4-methoxy-2-morpholinocarbonyl-4H-s-triazolo[1,5-a][1,4]benzodiazepine
30. 8-Chloro-6-(2-chlorophenyl)-4-hydroxy-N-methyl-4H-s-triazolo[1,5-a][1,4]benzodiazepine-2-carboxamide
31. 8-Chloro-4-methoxy-N-methyl-6-phenyl-4H-s-triazolo[1,5-a][1,4]benzodiazepine-2-carboxamide
32. 8-Chloro-6-(2-chlorophenyl)-4-hydroxy-N,N-dimethyl-4H-s-triazolo[1,5-a][1,4]benzodiazepine-2-carboxamide
33. 8-Chloro-4-methoxy-N,N-dimethyl-6-phenyl-4H-s-triazolo[1,5-a][1,4]benzodiazepine-2-carboxamide
34. 8-Chloro-4-hydroxy-2-(4-methylpiperazinocarbonyl)-6-phenyl-4H-s-triazolo[1,5-a][1,4[benzodiazepine
35. 8-Chloro-4-methoxy-2-(4-methylpiperazinocarbonyl)-6-phenyl-4H-s-triazolo[1,5-a][1,4]benzodiazepine
36. 8-Fluoro-6-(2-fluorophenyl)-4-hydroxy-4H-s-triazolo[1,5-a][1,4]benzodiazepine-2-carboxamide
37. 8-Fluoro-6-(2-fluorophenyl)-4-methoxy-4H-s-triazolo[1,5-a][1,4]benzodiazepine-2-carboxamide
38. 4-Methoxy-8-nitro-6-phenyl-4H-s-triazolo[1,5-a][1,4]benzodiazepine-2-carboxamide
39. 4-Methoxy-8-methyl-6-phenyl-4H-s-triazolo[1,5-a][1,4]benzodiazepine-2-carboxamide
40. 4,8-Dimethoxy-6-phenyl-4H-s-triazolo[1,5-a][1,4]benzodiazepine-2-carboxamide
41. 4-Methoxy-6-phenyl-8-trifluoromethyl-4H-s-triazolo[1,5-a][1,4]benzodiazepine-2-carboxamide
42. 8-Chloro-4-methoxy-N-(2-methoxyethyl)-6-phenyl-4H-s-triazolo[1,5-a][1,4]benzodiazepine-2-carboxamide
43. 8-Chloro-4-ethoxy-6-phenyl-4H-s-triazolo[1,5-a][1,4]benzodiazepine-2-carboxamide 44. 6-(2-Chlorophenyl)-4-methoxy-4H-s-triazolo[1,5-a][1,4]benzodiazepine-2-carboxamide
45. 4-Acetoxy-6-phenyl-4H-s-triazolo[1,5-a][1,4]benzodiazepine
46. 4-Acetoxy-8-chloro-6-phenyl-4H-s-triazolo[1,5-a][1,4]benzodiazepine
47. 4-Acetoxy-8-chloro-6-(2-chlorophenyl)-4H-s-triazolo[1,5-a][1,4]benzodiazepine
48. 4-Acetoxy-8-chloro-2-methyl-6-phenyl-4H-s-triazolo[1,5-a][1,4]benzodiazepine
49. 4-Acetoxy-8-chloro-6-(2-chlorophenyl)-2-methyl-4H-s-triazolo-[1,5-a][1,4]benzodiazepine
50. 4-Acetoxy-8-chloro-2-ethyl-6-phenyl-4H-s-triazolo[1,5-a][1,4]benzodiazepine
51. 4-Acetoxy-8-chloro-6-(2-chlorophenyl)-2-ethyl-4H-s-triazolo[1,5-a][1,4]benzodiazepine
52. 4-Acetoxy-8-chloro-6-(2,6-difluorophenyl)-4H-s-triazolo[1,5-a][1,4]benzodiazepine-2-carboxamide
53. 4-Acetoxy-8-chloro-6-phenyl-4H-s-triazolo[1,5-a][1.4]benzodiazepine-2-carboxylic acid
54. Ethyl 4-acetoxy-8-chloro-6-phenyl-4H-s-triazolo[1,5-a][1,4]benzodiazepine-2-carboxylate
55. Ethyl 4-acetoxy-8-chloro-6-(2-chlorophenyl)-4H-s-triazolo[1,5-a][1,4]benzodiazepine-2-carboxylate
56. 4-Acetoxy-8-chloro-6-phenyl-4H-s-triazolo[1,5-a][1,4]benzodiazepine-2-carboxamide
57. 4-Benzoyloxy-8-chloro-6-phenyl-4H-s-triazolo[1,5-a][1,4]benzodiazepine-2-carboxamide
58. 8-Chloro-6-phenyl-4-phenylacetyloxy-4H-s-triazolo[1,5-a][1,4]benzodiazepine-2-carboxamide
59. 8-Chloro-6-phenyl-4-propionyloxy-4H-s-triazolo[1,5-a][1,4]benzodiazepine-2-carboxamide
60. 4-Acetoxy-8-chloro-6-(2-chlorophenyl)-4H-s-triazolo[1,5-a][1,4]benzodiazepine-2-carboxamide
61. 4-Acetoxy-8-chloro-N-methyl-6-phenyl-4H-s-triazolo[1,5-a][1,4]benzodiazepine-2-carboxamide
62. 4-Acetoxy-8-chloro-6-(2-chlorophenyl)-N-methyl-4H-s-triazolo[1,5-a][1,4]benzodiazepine-2-carboxamide
63. 4-Acetoxy-8-chloro-N,N-dimethyl-6-phenyl-4H-s-triazolo[1,5-a][1,4]benzodiazepine-2-carboxamide
64. 4-Acetoxy-8-chloro-6-(2-chlorophenyl)-N,N-dimethyl-4H-s-triazolo[1,5-a][1,4]benzodiazepine-2-carboxamide
65. 4-Acetoxy-8-chloro-6-phenyl-2-piperidinocarbonyl-4H-s-triazolo[1,5-a][1,4]benzodiazepine
66. 4-Acetoxy-8-chloro-6-(2-chlorophenyl)-2-piperidinocarbonyl-4H-s-triazolo[1,5-a][1,4]benzodiazepine
67. 4-Acetoxy-8-chloro-2-morpholinocarbonyl-6-phenyl-4H-s-triazolo[1,5-a][1,4]benzodiazepine
68. 4-Acetoxy-8-chloro-6-(2-chlorophenyl)-2-morpholinocarbonyl-4H-s-triazolo[1,5-a][1,4]benzodiazepine
69. 4-Acetoxy-8-chloro-2-(4-methylpiperazinocarbonyl)-6-phenyl-4H-s-triazolo[1,5-a][1,4]benzodiazepine
70. 4-Acetoxy-8-fluoro-6-(2-fluorophenyl)-4H-s-triazolo[1,5-a][1,4]benzodiazepine-2-carboxamide
71. 4-Acetoxy-8-nitro-6-phenyl-4H-s-triazolo[1,5-a][1,4]benzodiazepine-2-carboxamide
72. 4-Acetoxy-8-methyl-6-phenyl-4H-s-triazolo[1,5-a][1,4]benzodiazepine-2-carboxamide
73. 4-Acetoxy-8-methoxy-6-phenyl-4H-s-triazolo[1,5-a][1,4]benzodiazepine-2-carboxamide
74. 4-Acetoxy-6-phenyl-8-trifluoromethyl-4H-s-triazolo[1,5-a][1,4]benzodiazepine-2-carboxamide
75. 4-Acetoxy-8-chloro-N-(2-methoxyethyl)-6-phenyl-4H-s-triazolo[1,5-a][1,4]benzodiazepine-2-carboxamide
76. 4-Acetoxy-6-(2-chlorophenyl)-4H-s-triazolo[1,5-a][1,4]benzodiazepine-2-carboxamide

EXAMPLE 1

A mixture of 1.06 g of 8-chloro-6-phenyl-4H-s-triazolo[1,5-a][1,4]benzodiazepine-2-carboxamide 5N-oxide 10 ml of acetic acid and 10 ml. of acetic anhydride is heated at 90 to 100° C for 1 hour. After evaporation of the solvent under reduced pressure, a small volume of ether is added to the residue, whereby 4-acetoxy-8-chloro-6-phenyl-4H-s-triazolo[1,5-a][1,4]benzodiazepine-2-carboxamide is obtained as crystals. Recrystallization from methanol yields colorless prisms melting at 222° to 224° C.

Elemental analysis: $C_{19}H_{14}ClN_5O_3$
Calculated: C57.65, H3.57, N17.70
Found: C57.64, H3.33, N17.56

EXAMPLE 2

To a solution of 0.8 g. of 4-acetoxy-8-chloro-6-phenyl-4H-s-triazolo[1,5-a][1,4]benzodiazepine in 8 ml. of methanol is added dropwise with stirring 1.1 ml. of a 2N aqueous sodium hydroxide solution, and after about 5 minutes the reatction mixture is acidified with acetic acid, followed by evaporation of the solvent under reduced pressure. To the residue is added water and the resulting precipitate is collected by filtration to obtain 8-chloro-4-hydroxy-6phenyl4H-s-triazolo[1,5-a][1,4]benzodiazepine-2-carboxamide as crystals. Recrystallization from a mixture of chloroform and methanol yields colorless needles melting at 235 to 240° C (3/2 hydrate).

Elemental analysis: $C_{17}H_{12}ClN_5O_2.3/2H_2O$
Calculated: C53.62, H3.97, N18.39
Found: C53.54, H3.65, N18.26

EXAMPLE 3

To a solution of 0.396 g. of 4-acetoxy-8-chloro-6-phenyl-4H-s-triazolo[1,5-a][1,4]benzodiazepine-2-carboxamide in 10 ml. of methanol are added two drops of concentrated sulfuric acid, and the mixture was refluxed for 5 minutes, followed by evaporation of methanol. The residue is neutralized with saturated aqueous sodium bicarbonate solution and the precipitated crystals are collected by filtration, washed with water and dried to obtain 8-chloro-4-methoxy-6-phenyl-4H-s-triazolo[1,5-a][1,4]benzodiazepine-2-carboxamide as crystals. Recrystallization from a mixture of chloroform and methanol yields colorless prisms (1/3 hydrate) melting at 264° to 267° C.

Elemental analysis: $C_{18}H_{14}ClN_5O_2.1/3H_2O$
Calculated: C57.83, H3.96, N18.74
Found: C57.94, H3.65, N18.70

EXAMPLE 4

To a solution of 0.38 g. of 8-chloro-4-hydroxy-6-phenyl-4H-s-triazolo[1,5-a][1,4]benzodiazepine-2-carboxamide (3/2 hydrate) in 5 ml. of pyrine is added 0.2 ml. of acetic anhydride and the mixture is left to stand at room temperature for 2 hours, followed by addition of water. The precipitated crystals are collected by filtration to yield 4-acetoxy-8-chloro-6-phenyl-4H-s-triazolo[1,5-a][1,4]-benzodiazepine-2-carboxamide as crystals. This product is identical with the product in Example 1 with respect to melting point and infrared absorption spectrum.

EXAMPLE 5

To a solution of 8-chloro-4-hydroxy-6-phenyl-4H-s-triazolo[1,5-a][1,4]benzodiazepine-2-carboxamide (3/2 hydrate) in methanol is added a small amount of concentrated sulfuric acid, and the mixture is treated in the same manner as that of Example 3 to give 8-chloro-4-methoxy-6-phenyl-4H-s-triazolo[1,5-a][1,4]benzodiazepine-2-carboxamide as crystals (1/3 hydrate). This product is identical with the product in Example 3 with respect to melting point and infrared absorption spectrum.

EXAMPLE 6

An example of practical recipe in which a compound of this invention is utilized as tranquilizer is as follows:

Tablet

| (1) | 8-chloro-4-methoxy-6-phenyl-4H-s-triazolo-[1,5-a][1,4]benzodiazepine-2-carboxamide | 1 | mg |
|---|---|---|---|
| (2) | lactose | 73 | mg |
| (3) | corn starch | 40 | mg |
| (4) | hydroxypropyl cellulose | 5.5 | mg |
| (5) | magnesium stearate | 0.5 | mg |
| | | 120.0 | mg per tablet |

(1), (2), 9/10 quantity of (3), and (4) are thoroughly mixed and the mixture is granulated by wet granulation method. Remaining quantity of (3), and (5) are added to the granules and compresses into tablets. Thus prepared tablets may further be coated with suitable coating materials, e.g. sugar.

What we claim is:

1. A compound of the general formula (I):

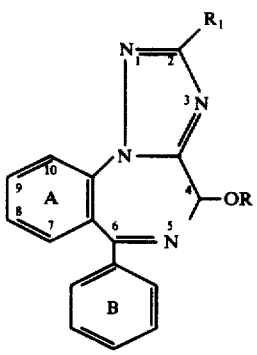

wherein $R_1$ represents a hydrogen atom, cyclopropylmethyl, cyclopentyl, cyclohexyl, an alkyl group of from 1 to 6 carbon atoms, carboxyl, -COOR$_3$ wherein $R_3$ is alky of from 1 to 4 carbon atoms, or

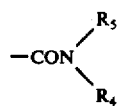

wherein each of $R_4$ and $R_5$ are hydrogen, alkyl of from 1 to 6 carbon atoms, alkyl substituted with alkoxy groups having from 1 to 4 carbon atoms said alkyl group having 1 to 6 carbon atoms, and wherein $R_4$ and $R_5$ join to form with the nitrogen a 5 to 7 membered heteroxyclic ring selected from the group consisting of pyrrolidine, piperidine, homopiperidine, morpholine, N-alkylpiperazine having 1 to 3 carbon atoms in the alkyl group, and N-(2-methoxyethyl) piperazine and wherein R is a hydrogen atom, a lower alkyl having 1 to 4 carbon atoms, an acyl group -COR$_6$ wherein R$_6$ is phenyl, tolyl, benzyl, phenethyl or a lower alkyl group having 1 to 4 carbon atoms, and each of the rings A and B is unsubstituted or substituted by a halogen atom, nitro, lower alkyl having 1 to 4 carbon atoms, trifluoromethyl or a lower alkoxy group having 1 to 4 carbon atoms, and the pharmaceutically acceptable acid addition salts thereof.

2. A compound as claimed in claim 1, wherein $R_1$ is

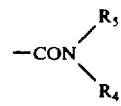

wherein $R_4$ and $R_5$ are as set out above.

3. A compound as claimed in claim 2 wherein $R_1$ is a carboxamide (—CONH$_2$) group.

4. A compound as claimed in claim 2, wherein R is hydrogen atom.

5. A compound as claimed in claim 2, wherein R is an acyl group -COR$_6$ wherein R$_6$ is lower alkyl having 1 to 4 carbon atoms, phenyl, tolyl, benzyl and phenethyl.

6. A compound as claimed in claim 5, wherein the acyl group is acetyl group.

7. A compound as claimed in claim 2, wherein R is a lower alkyl group having 1 to 4 carbon atoms.

8. A compound as claimed in claim 4, wherein the rings A and/or B are substituted by a halogen atom.

9. A compound as claimed in claim 4, wherein the ring A is substituted by a halogen atom and the ring B is unsubstituted.

10. 8-chloro-4-hydroxy-b 6-phenyl-4H-s-triazolo[1,5-a][1,4]benaodiazepine-2-carboxamide.

11. 4-acetoxy-8-chloro-6-phenyl-4H-s-triazolo[1,5-a][1,4]benzodiazepine-2-carboxamide.

12. 8-chloro-4methoxy-6-phenyl-4H-s-triazolo[1,5-a][1,4]benezodiazepine-2-carboxamide.

13. A compound according to claim 8, in which Ring A is substituted at the 8 position by halogen and Ring B is halogen substituted in the ortho position.

14. A compound according to claim 6, in which the rings A and/or B are substituted by a halogen atom 15. A compound according to claim 7, in which the rings A and/or B are substituted by a halogen atom 16. A compound according to claim 6, in which Ring A is substituted by a halogen atom and Ring B is unsubstituted.

17. A compound according to claim 7, in which Ring A is substituted by a halogen atom and Ring B is unsubstituted.

* * * * *